US006558947B1

(12) United States Patent
Lund et al.

(10) Patent No.: US 6,558,947 B1
(45) **Date of Patent: *May 6, 2003**

(54) THERMAL CYCLER

(75) Inventors: Kurt Lund, Del Mar, CA (US); Barry E. Rothenberg, Del Mar, CA (US)

(73) Assignee: Applied Chemical & Engineering Systems, Inc., Del Mar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/643,479

(22) Filed: Aug. 22, 2000

Related U.S. Application Data

(63) Continuation-in-part of application No. 08/939,029, filed on Sep. 26, 1997, now Pat. No. 6,106,784.

(51) Int. Cl.[7] ................................................ C12M 1/38

(52) U.S. Cl. ............................... 435/303.1; 435/286.1; 435/288.4; 435/809; 422/104; 219/428

(58) Field of Search ........................... 435/286.1, 287.2, 435/288.4, 303.1, 809; 422/99, 102, 104; 219/428

(56) References Cited

U.S. PATENT DOCUMENTS

| | | | | |
|---|---|---|---|---|
| 3,556,731 | A | | 1/1971 | Martin |
| 4,116,777 | A | | 9/1978 | Takatsy et al. |
| 4,208,574 | A | | 6/1980 | Schafer |
| 4,865,986 | A | * | 9/1989 | Coy et al. |
| 4,877,134 | A | | 10/1989 | Klein |
| 4,919,894 | A | | 4/1990 | Daniel |
| 4,950,608 | A | * | 8/1990 | Kishimoto |
| 5,096,672 | A | | 3/1992 | Tervamaki et al. |
| 5,100,623 | A | | 3/1992 | Friswell |
| 5,158,132 | A | | 10/1992 | Guillemot |
| 5,435,378 | A | | 7/1995 | Heine et al. |
| 5,459,300 | A | | 10/1995 | Kasman |
| 5,504,007 | A | | 4/1996 | Haynes |
| 5,525,300 | A | | 6/1996 | Danssaert et al. |
| 5,601,141 | A | | 2/1997 | Gordon et al. |
| 5,604,130 | A | | 2/1997 | Warner et al. |
| 5,705,062 | A | | 1/1998 | Knobel |
| 6,106,784 | A | * | 8/2000 | Lund et al. |

FOREIGN PATENT DOCUMENTS

| | | | | |
|---|---|---|---|---|
| DE | 39 41 168 | A | * | 6/1990 |
| GB | 2 333 250 | A | * | 7/1999 |

* cited by examiner

*Primary Examiner*—William H. Beisner
(74) *Attorney, Agent, or Firm*—Fulwider Patton Lee & Utecht, LLP

(57) ABSTRACT

A thermal cycling device for a titration plate enables selected sample wells to be individually subjected to heating and cooling cycles independent of the temperature of adjacent sample wells. Each sample well is fitted with its own mechanism for independently heating and cooling the sample therein while a heat sensing mechanism provides feedback to the controller. The device is especially well adapted for enabling elected samples in a single titration plate to be simultaneously subjected to different PCR programs.

11 Claims, 14 Drawing Sheets

THERMAL CYCLER

This application is a continuation-in-part of application Ser. No. 08/939,029 filed on Sep. 26, 1997, now U.S. Pat. No. 6,106,784.

BACKGROUND OF THE INVENTION

The present invention generally relates to a thermal cycler for titration plates and more particularly pertains to a device that is capable of controlling the temperature of the contents of individually selected sample wells within a multi-well titration plate.

The Polymerase Chain Reaction (PCR) process effects the replication of long-chain DNA molecules and is today an essential tool in genetics and molecular biology. It is the central component in diagnostics, therapeutics and genomics involving DNA amplification. The process is commenced with a denaturing step typically at 95C at which point strands of the DNA double helix in a solution are separated. After time to equilibrate, the temperature is rapidly reduced to the annealing temperature (typically, 50 to 65C) where primers hybridize to the two separated DNA strands. Thus attached, the primers allow the formation of new DNA at the optimum synthesis temperature (typically, 72C), where the chain-length of the DNA produced depends on the time held at this temperature. To double the molecules produced, the temperature cycle is repeated. Thus, a single molecule of DNA will result in 34 billion copies after 35 cycles ($2^{35}$)

Titration plates are commonly employed in laboratory work of various disciplines to store multiple samples, typically in a closely spaced 8×12 pattern of sample wells. The titration plate is often of monolithic construction and may comprise a single injection molding of a chemically inert plastic material. Each individual well extends downwardly from the flat top face of the plate, is typically cylindrical in cross-section and is provided with a flat, U-shaped or V-shaped bottom to support a sample volume of 1 ml.

Titration plates offer a convenient means for processing large numbers of samples and are used to subject samples to PCR and DNA amplification. A distinct disadvantage inherent in the use of a titration plate as described above for such application is that heretofore thermal cyclers have typically utilized a single temperature block such that all samples contained in a single titration plate must execute the same PCR program simultaneously. An additional disadvantage is inherent in the fact that single temperature block type devices may be subject to a temperature gradient within the block which may adversely affect the process.

A simple hot plate fulfills the most fundamental requirements while the more sophisticated heating devices have included features that endeavor to maintain as uniform a temperature as possible throughout the entire array of samples contained in a titration plate. Additionally, heating devices are known that subject the entire array of sample wells in a titration plate to a repetition of prescribed temperature gradients as is useful for PCR.

The prior art is devoid of a device that is capable of subjecting selected individual sample wells in a titration plate to PCR and DNA amplification techniques, independent of the temperatures of neighboring or unselected wells.

SUMMARY OF THE INVENTION

The present invention provides a heating apparatus that is capable of controlling the temperature of individual sample wells in a titration plate without affecting the temperature of neighboring sample wells. Moreover, the device of the present invention is capable of simultaneously subjecting individual sample wells of a titration plate to different temperatures and different rates of temperature change.

A programmable controller is employed to control the operation of each heating and cooling mechanism associated with each sample well. The use of a temperature sensor associated with each sample well that feeds temperature data back to the controller allows for more precise control of the temperature to yield high PCR efficiency. Different PCR temperature programs (cycles) or experiments can thereby be exercised in different wells of the same plate at the same time.

Preferred embodiments of the present invention may include an array of sleeves that are arranged and dimensioned to individually receive each of the sample wells of a titration plate placed thereover. Such sleeves may serve to direct or conduct heat to the well received therein and may optionally be relied upon to conduct heat away from the vial when not in the heating mode. Alternatively, the sleeves may be relied upon to merely properly position sample wells inserted thereinto relative to a source of conducted, convected or radiated heat. As a further alternative, the selective heating may be accomplished without the use of individual well receiving sleeves.

In a preferred embodiment, an array of thermally conductive sleeves extend upwardly from a cold plate which serves to conduct heat away from each sample well via the corresponding sleeve. Each sleeve is additionally fitted with an individually controllable heating element. By energizing such heating element, the thermally conductive sleeve conducts heat to the corresponding sample well to heat the material contained therein. Adjacent sample wells are unaffected by the heat generated by the energized heating element and continue to be maintained in their original state by virtue of their continued interconnection to the cold plate via their corresponding sleeves. Optionally, the sleeve is physically disconnected from the cold plate upon energization of the corresponding heating element to minimize heat loss and thereby expedite the heating process. A programmable controller is employed to enable an operator to select those heating elements which are to be energized.

In alternative embodiments, the exterior surface of each sample well is coated with a resistive material and the sleeve serves to conduct electricity thereto. As a result, heating is effected on the well itself. Alternatively, each sleeve is in direct contact with an individually controllable Peltier-effect device with which both the heating as well as cooling of each well is accomplished. As a further alternative, a source of radiant energy such as a laser is focused on each well wherein selective energization thereof serves to heat selected sample wells. Finally, the sleeve may be relied upon to direct a flow of heated fluid at each well to effect a heating thereof.

In a further alternative embodiment of the present invention, variable thermal contact with a cold plate is effected by bimetallic elements. In its deactivated state, the bimetallic element conducts heat from the sample to the cold plate. As the heating element is energized, the heat is transferred to both the sample as well as the bimetallic element which causes the later to deflect thereby breaking thermal contact with the cold plate. A shape memory material such as Nitinol can be substituted for the bimetallic element.

In any of the various embodiments of the present invention, separate temperature sensors may be associated with each individual sample well to provide feedback to the controller. Alternatively, a sensor mass may be associated with each sleeve to effect temperature measurement feedback for the thermal control. By appropriate adjustment of the sensor mass and its thermal resistance to the sleeve, its temperature can be shown to be dynamically equivalent to the solution temperature. As a further alternative, the temperature sensor may take the form of an integrated circuit mounted on a printed circuit board. The chip is in contact with a wing of the sleeve which extends into the void region between the wells and which acts as a thermal mass for dynamic similarity with the solution temperature.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The device of the present invention is used to alter the temperature of material contained in selected individual sample wells of a titration plate without affecting the temperature of the balance of the samples in the titration plate. This allows selected samples to be subjected to PCR programs and further allows different samples to be subjected to different PCR programs.

Figure 1:
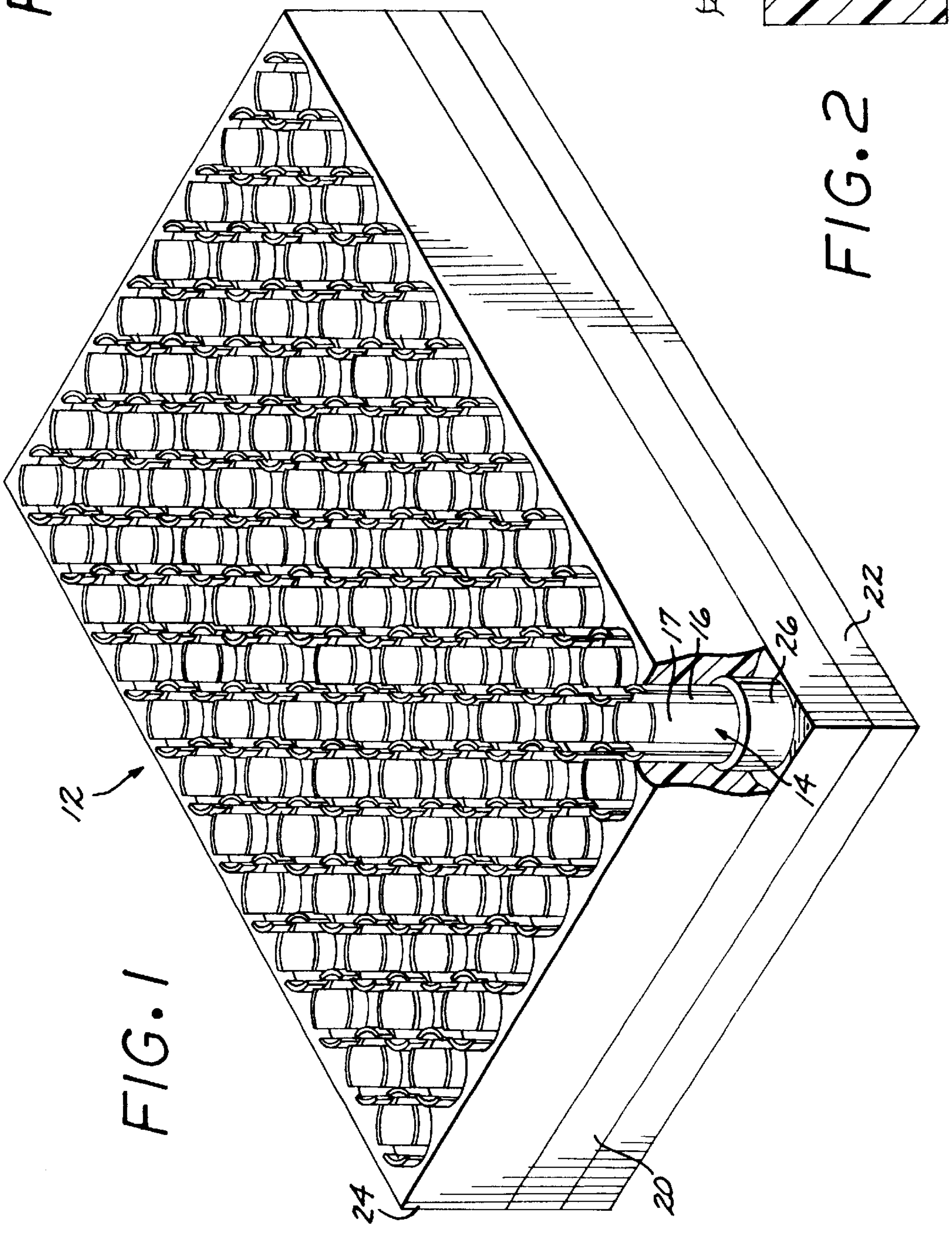
FIG. 1 is a partially cut back perspective view of the thawing device of the present invention.

FIG. 1 is a perspective view of a preferred embodiment 12 of the present invention. The particular embodiment shown comprises a heating device 12 which accommodates a titration plate having 96 sample wells arranged in an 8×12 pattern, with 9 mm on-center spacing. A different titration plate configuration would require a correspondingly configured heating device. The device supports an array of individual sleeves 14 that are dimensioned and arranged to receive the individual sample wells extending downwardly from a titration plate. Each sleeve is slotted 16 to accommodate reinforcing webs in the titration plate, and which in concert with the inherent resiliency of the material from which the sleeve is formed, enables the fingers 17 defined by the sleeve to act as leaf springs and to in effect grasp a sample well 18 inserted thereunto. In an effort to ensure that uniform contact pressure is exerted by the sleeve or fingers on the length of a sample well inserted thereinto, the distal end of each finger is curved slightly inwardly (1/32") in accordance with elementary beam theory. In this particular embodiment, each sleeve serves to conduct heat to and from the individual well received therein and due to the commensurate thermal conductivity and resiliency requirements, the sleeves are preferably formed of beryllium-copper alloy which is a widely used material for applications requiring good thermal or electrical conductivity, and good resiliency. Other preferred materials are nickel and aluminum alloys.

Each sleeve is in intimate and therefore thermal contact with a cold plate 20 situated therebelow that spans the entire device. Heat is actively removed from the cold plate, preferably by electronic means such as by a Peltier effect device or by more conventional means such as by the circulation of refrigerated coolant therethrough. The entire assembly is supported on a thermally insulative base 22 which may be furnished with a non-slip bottom surface.

Figure 2:
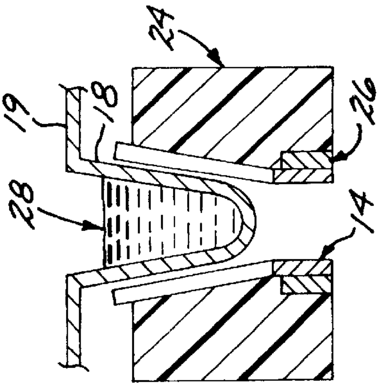
FIG. 2 is a cross-sectional view of an individual sample well received within a portion of the thawing device of the present invention.

As is visible in FIG. 2, surrounding each sleeve is a mass of thermally insulative material 24 such as an elastomer, which not only serves to thermally isolate the various sleeves and hence sample wells from one another, but may additionally be relied upon to provide additional resilience to the slotted portion of the sleeves to thereby enhance the grasping force generated thereby. Fitted about the base of each sleeve is a heating element which is individually energizeable. In its simplest form, a 1–10 watt winding of resistance wire within an electrically insulated shell is disposed in thermal contact with the circumference of the sleeve.

Figure 3:
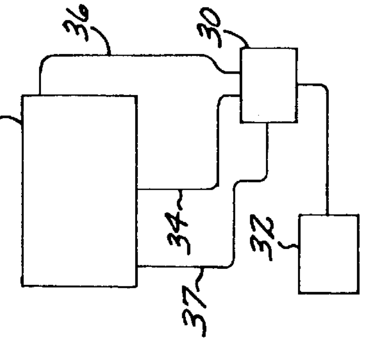
FIG. 3 is a schematic illustration of a complete heating system.

FIG. 3 generally illustrates the system as a whole wherein a fully programmable controller 30 allows an operator to select which sample wells are to be subjected to which program of heating and cooling. The controller alternately routes power from the power source 32 to a heating mechanism via 34 or optionally, to a cooling mechanism via 36 associated with a particular sample well. Information regarding the temperature of such sample well is fed back to the controller via conduit 37. The details associated with the programmable controlling of the flow of power to activate the individual heating and cooling mechanisms are well known to those skilled in the art as is the use of a feedback loop to provide precise control of temperature.

Figure 4:
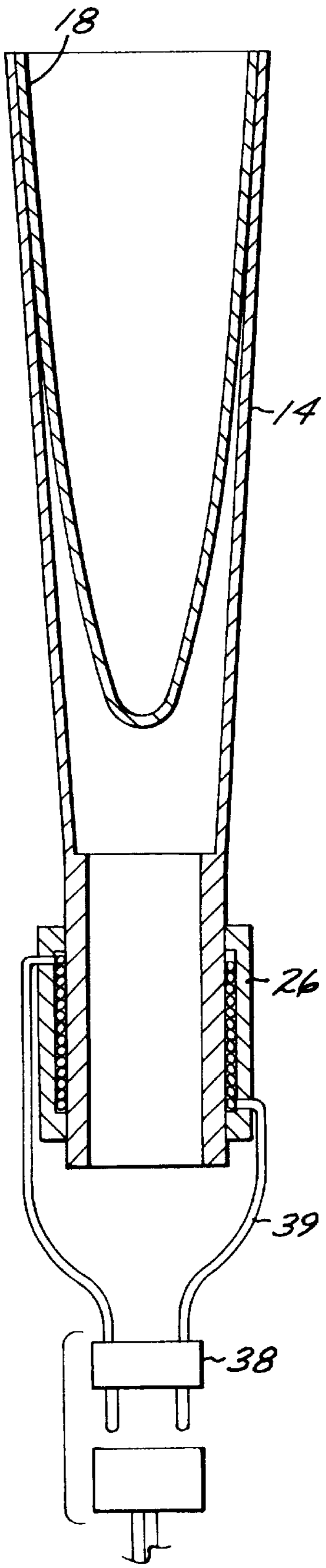
FIGS. 4–12 are semi-schematic representations of alternative embodiment heat source configurations.
Figure 5:
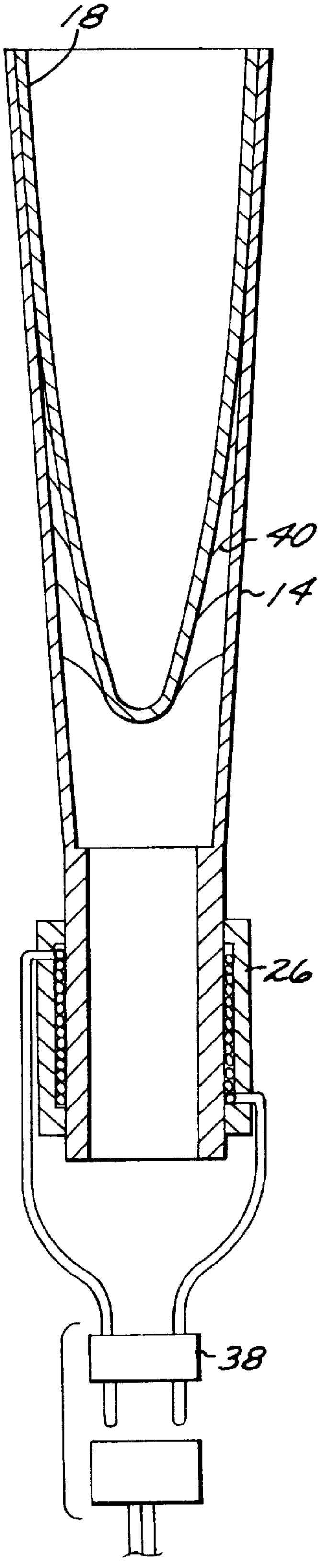
Figure 6:
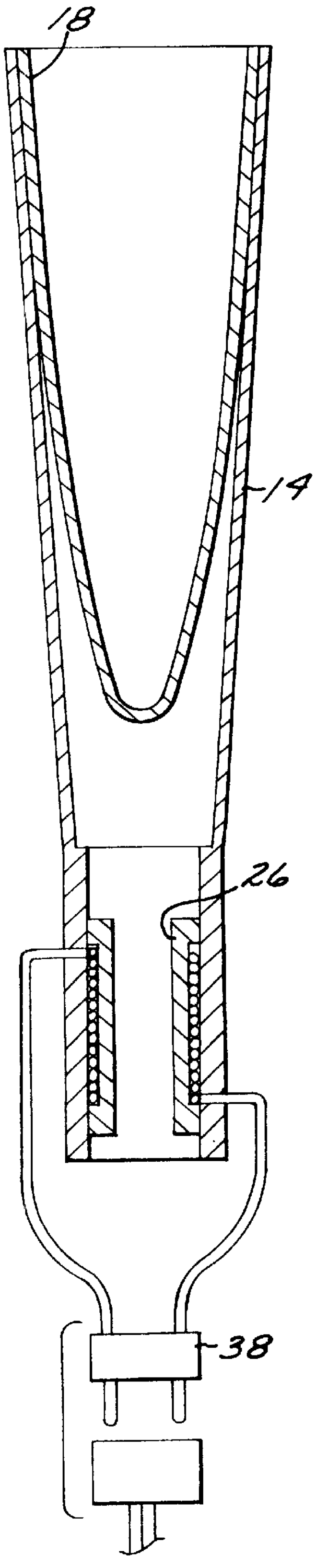

FIGS. 4–12, illustrate alternative embodiments that serve to exemplify a variety of different configurations by which an individual sample well is heatable in accordance with the present invention. The fact that the sleeves are shown making only marginal contact with the sample wells is for clarity only. In actuality, a substantial contact area is achieved. FIG. 4, is very similar to the configuration shown in FIG. 2 and additionally shows a connector 38 by which power is conducted to the heating element 26 and which facilitates replacement of the component in the event of failure. FIG. 5 illustrates the inclusion of fiber flock within sleeve 14 to facilitate heat transfer between the sample well 18 and sleeve 14. Material suitable for such use includes commercially available, high-conduction carbon fibers. FIG. 6 illustrates an alternative embodiment wherein the heater element 26 is fitted to the interior of sleeve 14. Such configuration provides for the more efficient use of heat generated by the heating element as substantially all heat radiated by the element is contained within the sleeve.

Figure 7:
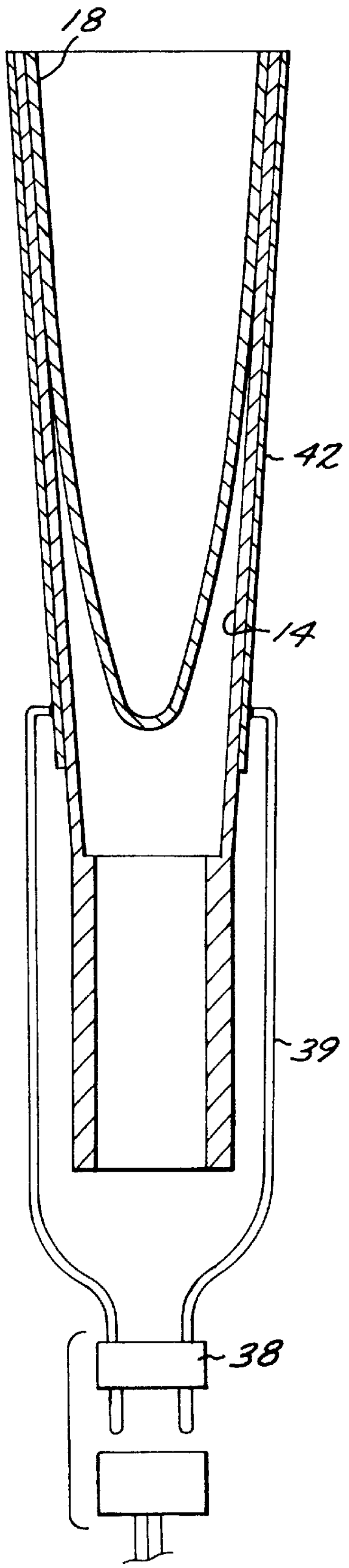
Figure 8:
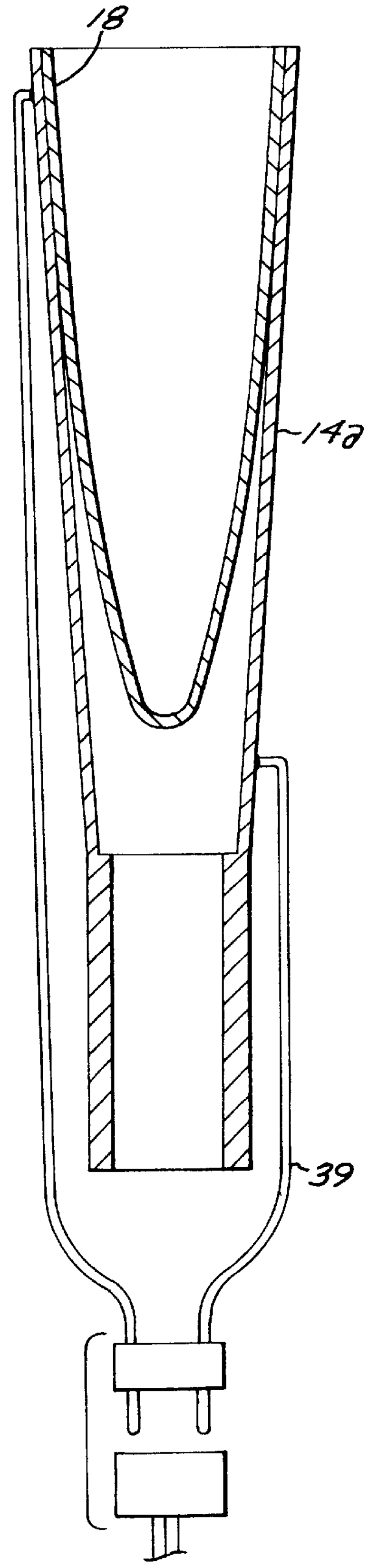
Figure 9:
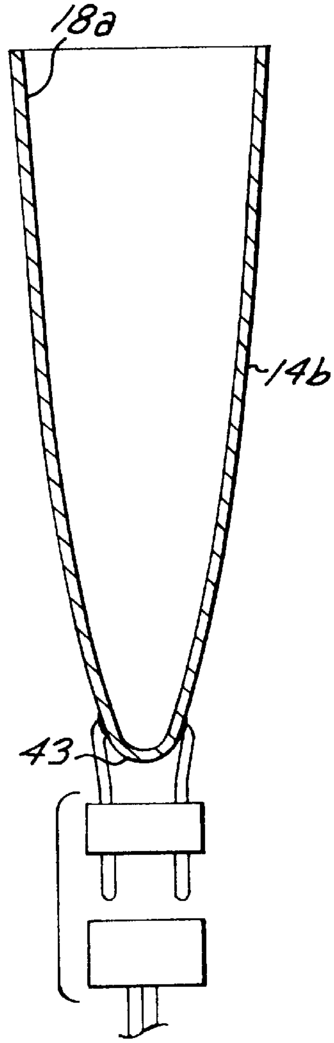

FIG. 7. illustrates an alternative embodiment wherein the sleeve 14 has a patterned heating foil 42 attached directly to its exterior surface. Conduits 39 are electrically interconnected to such foil. FIG. 8 provides an alternative wherein the sleeve 14*a* itself is formed of resistance material wherein energization via conduit 39 causes the sleeve to serve as the heating element. FIG. 9 illustrates an embodiment wherein the heating element 43 is coated directly onto the sample well 18*a* and wherein the sleeve 14*b* serves to conduct electricity to the coating. Energization thereof causes the sample well to heat up directly.

Figure 10:
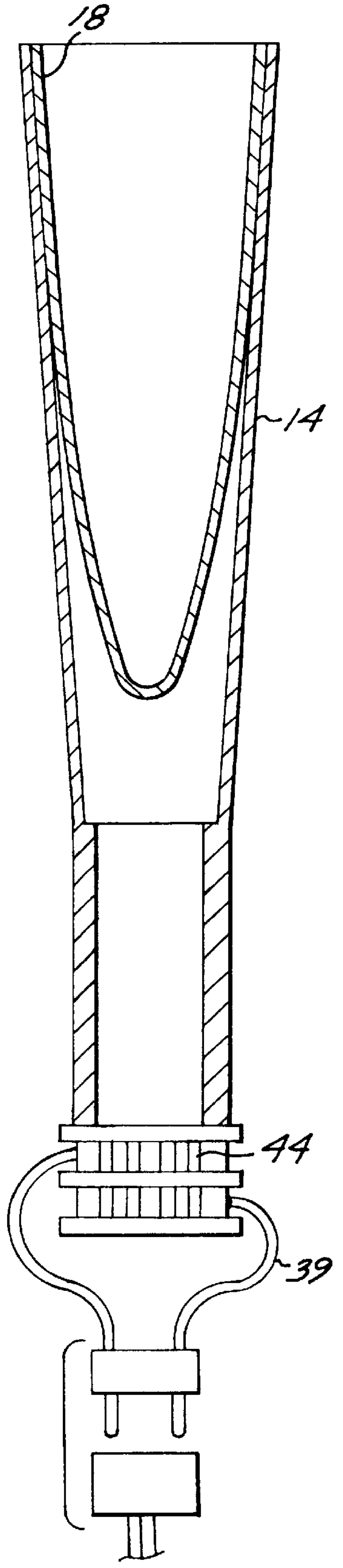

FIG. 10 illustrates an alternative embodiment wherein sleeve 14 is positioned in thermal contact with a Peltier device 44. Flow of current through conduits 39 in one direction causes the Peltier device to heat up while reversal of the flow of electrical current therethrough causes the Peltier device to cool. The selective cooling and heating of the various sample wells is thereby controlled by simply controlling the direction of current supplied to the various Peltier devices.

Figure 11:
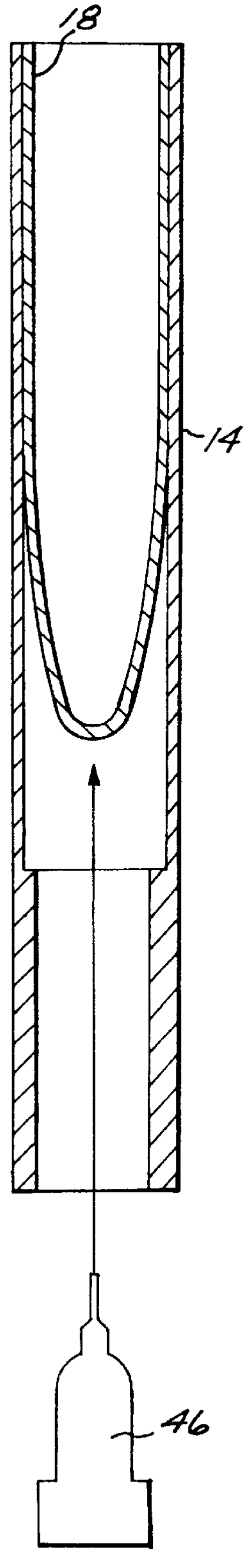

FIG. 11 illustrates an alternative embodiment wherein heating of the sample well 18 is accomplished by the absorption of radiant energy. A source of radiant energy such as a laser 46 is focused through the sleeve 14 so as to impinge on the sample well. The well may optionally be coated with absorbing material to enhance efficiency. The heating of a selected sample well may be accomplished by the selective energization of a corresponding laser, optical fiber or by the relative translational movement between the entire device 12 and a single laser.

Figure 12:
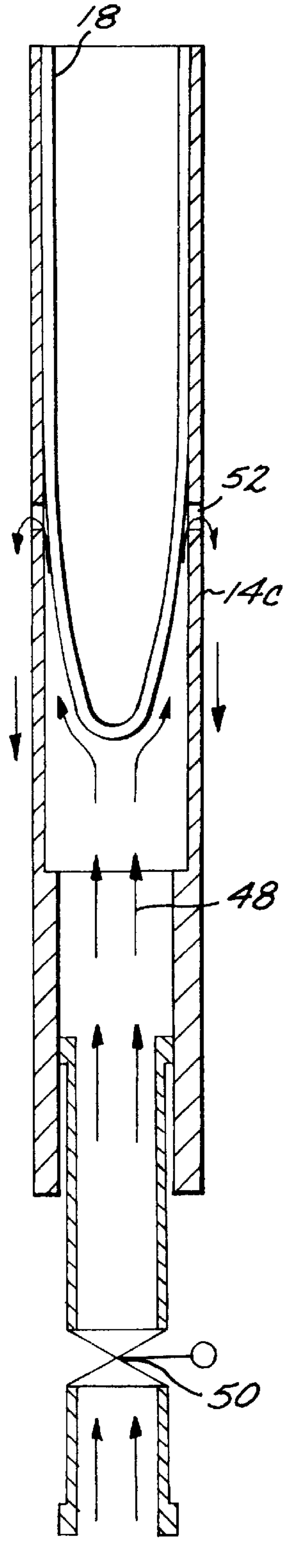

FIG. 12 illustrates an alternative embodiment wherein the sample well is heated by convection in that the flow of a heated fluid 48, such as air, is directed at the sample well to effect the heating thereof. The flow of heated fluid is controlled by valve 50 and is emitted near the base of the sample well 18 within sleeve 14*c*. Flowing upwardly, the flow impinges on the sample well to effect a transfer of heat and subsequently escapes through port 52 in the sleeve 14*c*.

Figure 13:
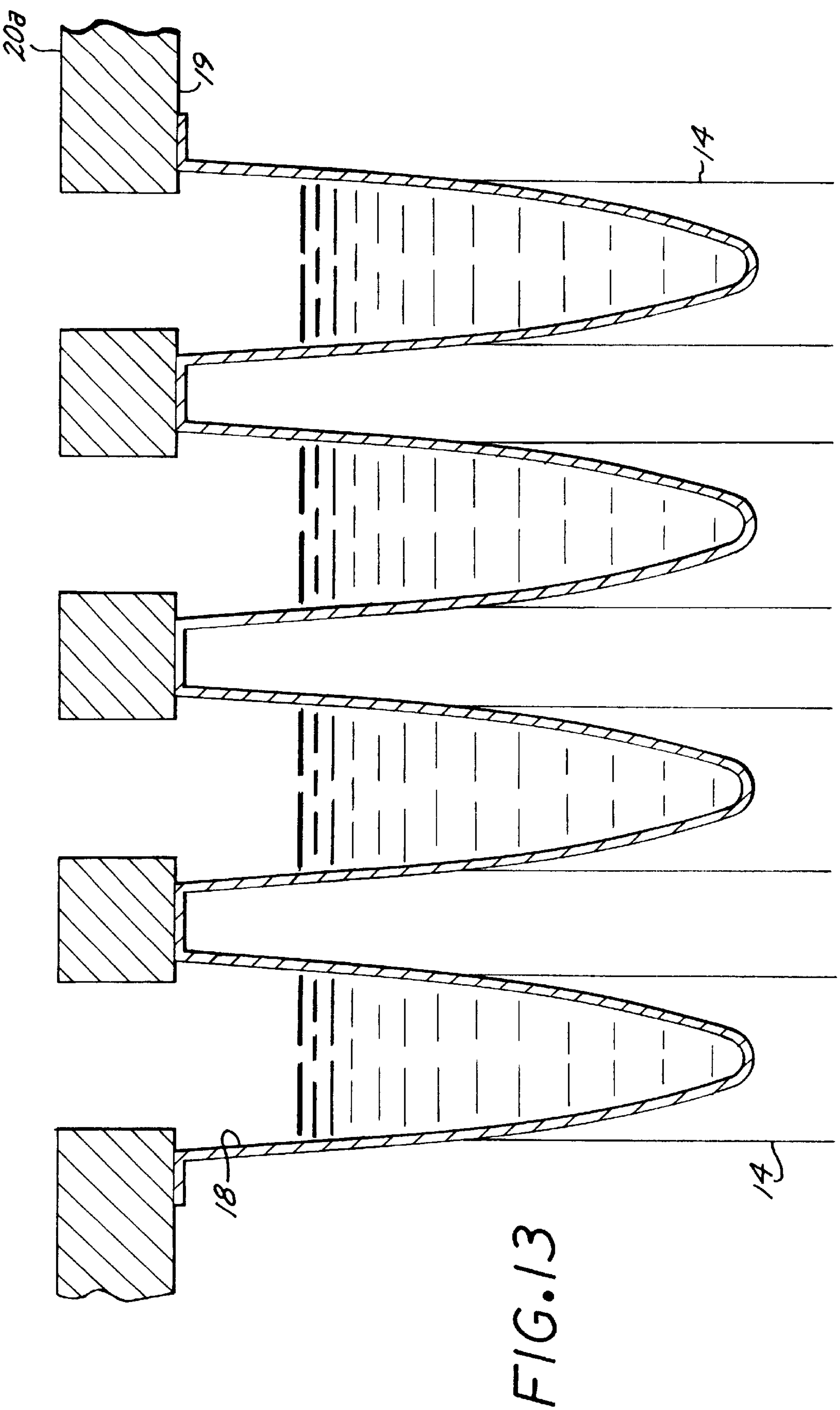
FIG. 13 is a cross sectional view of an alternative embodiment configuration.

As a further alternative to the particular configuration illustrated in FIG. 1, FIG. 13 provides for a cold plate 20*a* to be positioned above the titration plate 19. Heat is thereby transferred as it naturally rises above the sample wells 18.

Figure 14A:
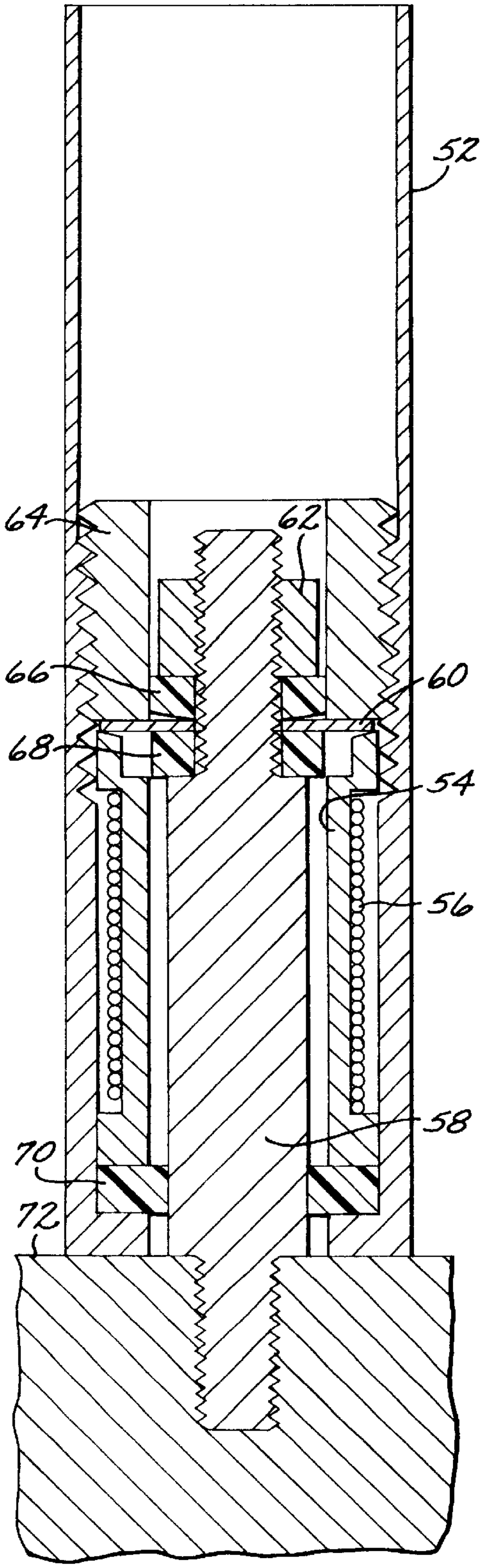
FIGS. 14*a* and *b* are cross-sectional views of an alternative embodiment incorporating a passive decoupling mechanism.
Figure 14B:
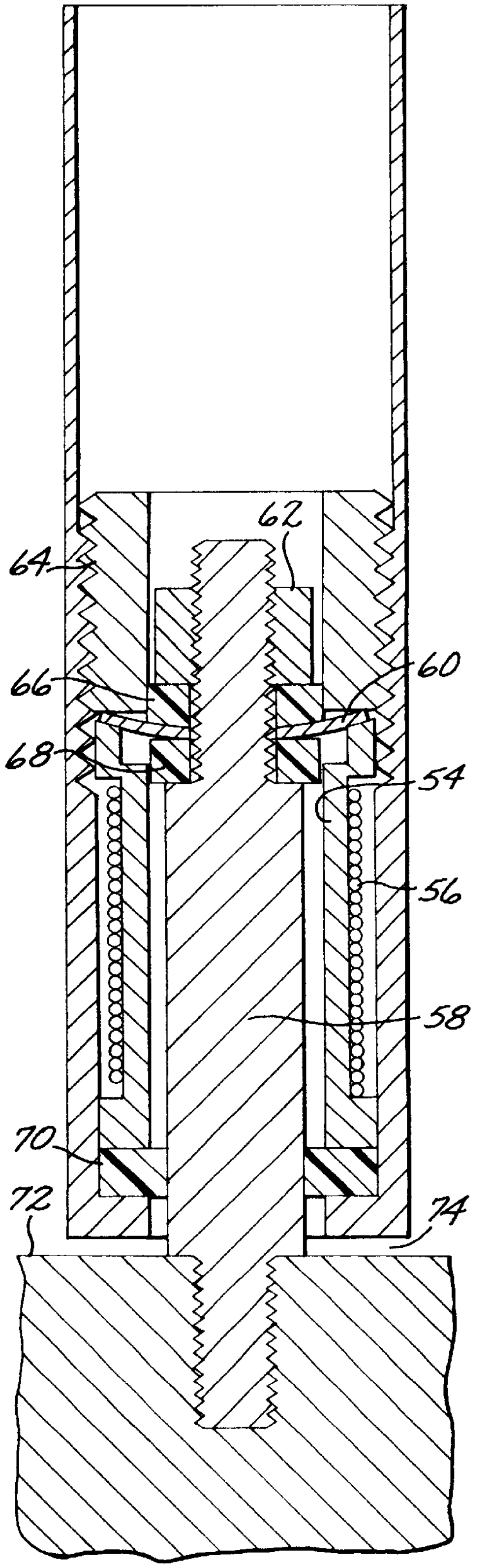

In alternative embodiments, a decoupling mechanism is associated with each sleeve. FIGS. 14*a* and *b* illustrate a configuration wherein the sleeve 52 and an internally disposed spool 54 of resistance wire 56 is slidably received on a support shaft 58. A bimetallic deflection disc 60 is rigidly affixed about the support shaft by a first nut 62 threaded thereunto. The periphery of the disc is attached to the sleeve by being sandwiched between the spool and a second nut 64. Insulating spacers 66, 68, 70 serve to thermally insulate the shaft from the sleeve. In its unactivated state shown in FIG. 14*a*, the bottom of the sleeve is in contact with the cold plate 72 situated therebelow. Upon energization of the resistance wire, the disc heats up (FIG. 14*b*), deflects and causes the sleeve to rise and become spaced apart (74) from the cold plate. Heat continuing to be generated by the resistance wire heats up the sleeve and a sample well received therein. Upon deenergization of the heating element, the bimetallic deflection disc cools to resume its original shape which causes the sleeve to be lowered back on to the cold plate which draws heat out of the sleeve and sample well to cool the sample.

Figure 15A:
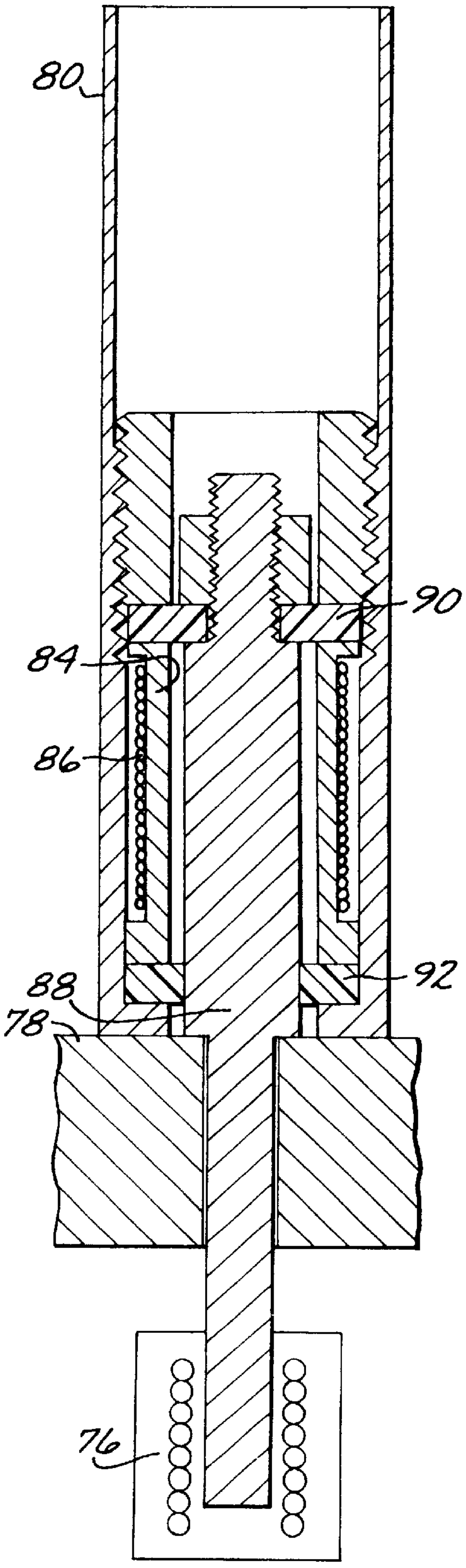
FIGS. 15*a* and *b* are cross-sectional views of an alternative embodiment incorporating an active decoupling mechanism.
Figure 15B:
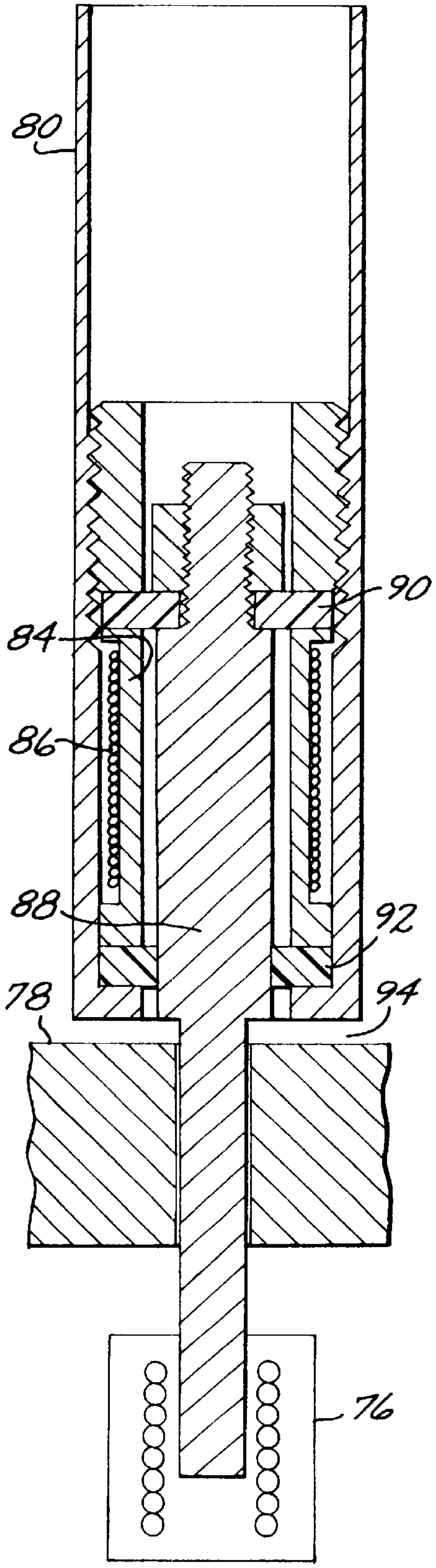

FIGS. 15*a* and *b* illustrate an active decoupling mechanism wherein a solenoid or other actuator 76 situated below the cold plate 78 lifts the sleeve 80 off of the cold plate upon activation. The sleeve and associated spool 84 of resistance wire 86 is rigidly affixed to a plunger 88 that extends from the solenoid through the cold plate. Insulating spacers 90, 92 serve to thermally insulate the plunger from the sleeve. In its unactivated state shown in FIG. 15*a*, the sleeve rests atop the cold plate to draw heat from the sleeve and any sample well received therein. Activation of the solenoid (FIG. 15*b*) causes the sleeve and associated heating element to lift off (94) of the cold plate and break thermal contact. The heating element may be simultaneously activated with the solenoid. Upon deactivation, the sleeve settles back down on to the cold plate to reestablish thermal contact therewith. As a further alternative, the solenoid windings may serve as the heat source, whereby deletion of insulation spacers 90, 92 would allow the plunger 88 to conduct heat to the sleeve 80. As yet a further alternative, the solenoid or actuator 76 may be located above the cold plate 78 or be integral with sleeve 80.

Figure 16:
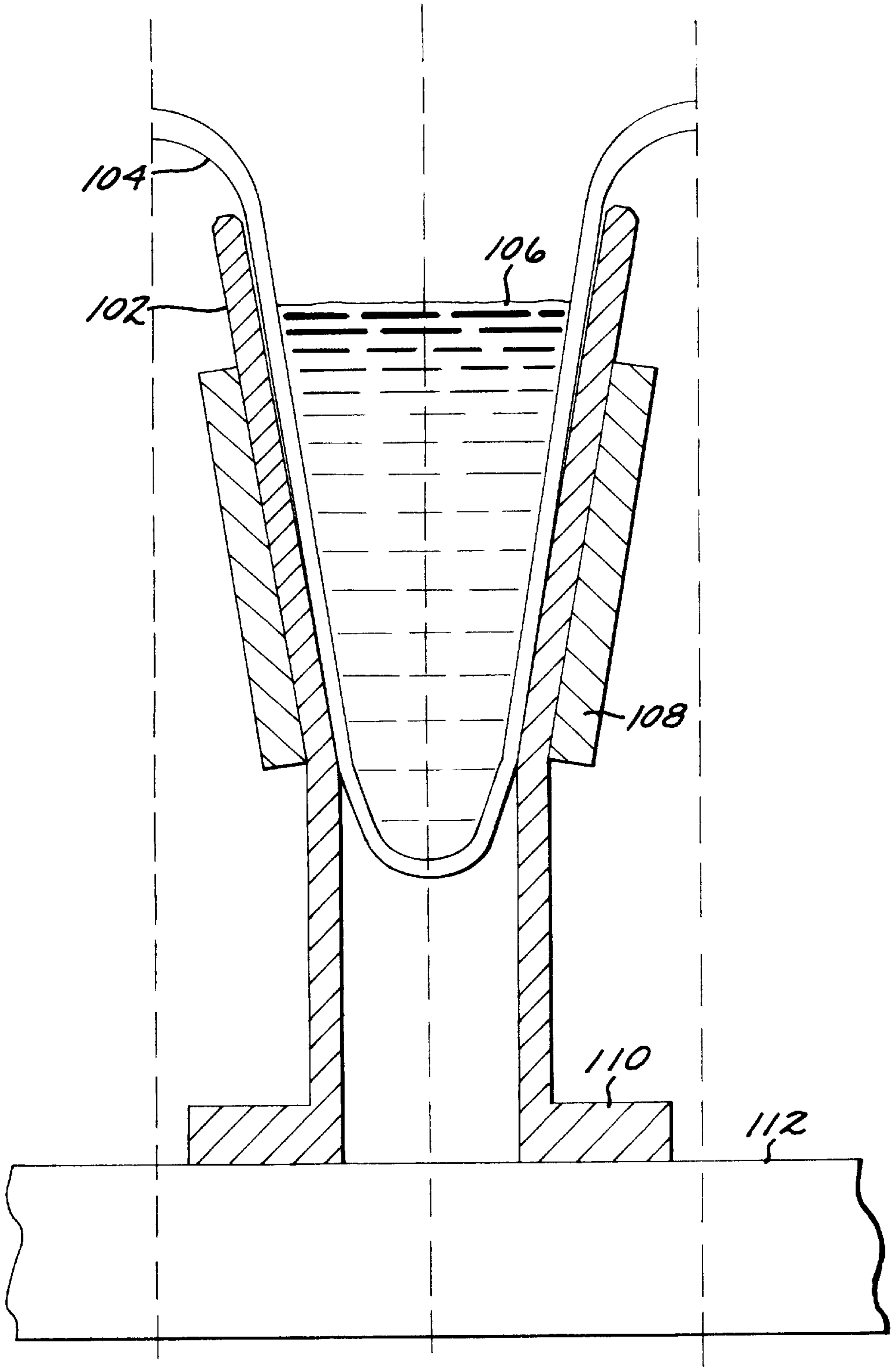
FIG. 16 is a cross-sectional view of an alternative embodiment of the present invention.

FIG. 16 is a cross-sectional view of another alternative embodiment of the present invention. The sleeve 102 is shown as a conical receptacle for the sample well 104 that contains sample 106. Surrounding the sleeve is heater element 108. The sleeve has a foot 110 which is in contact with cold plate 112 which is maintained or maintainable at a suitably low temperature. Any of various sensor elements may be integrated in this particular thermal cycler configuration.

Figure 17:
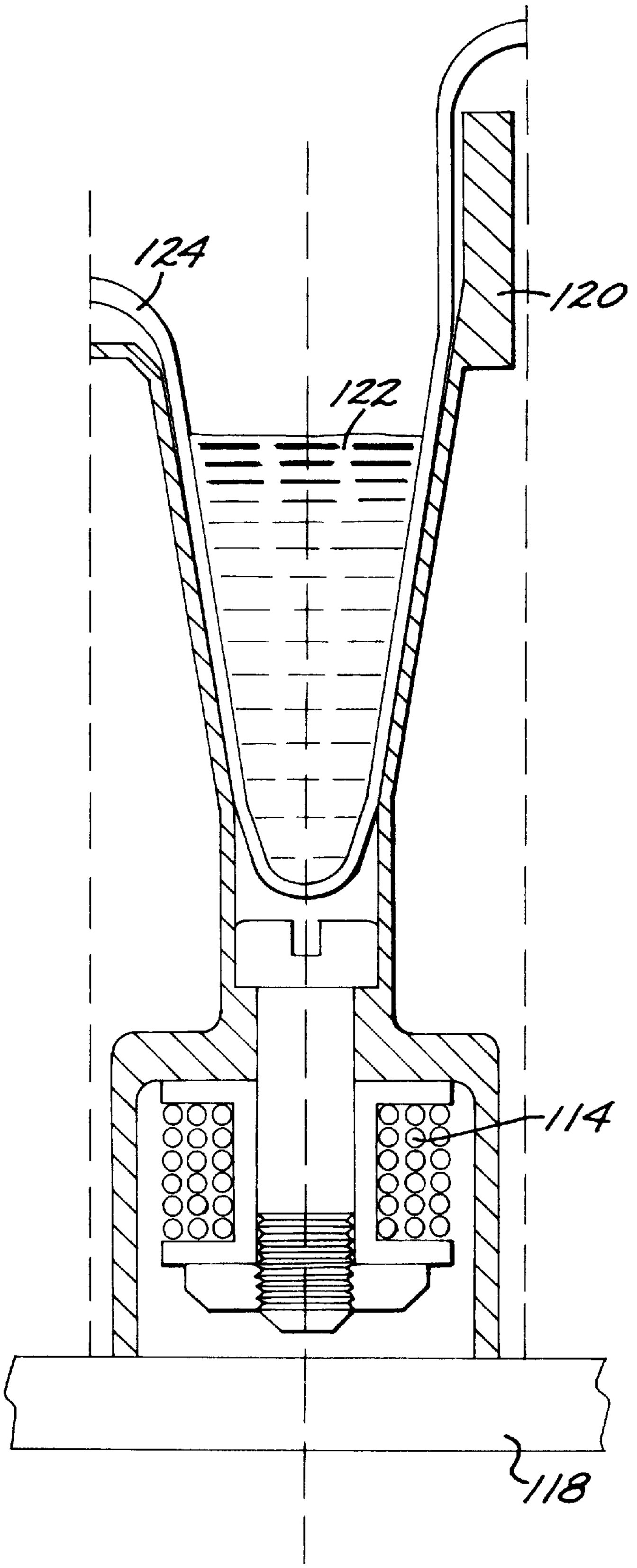
FIG. 17 is a cross-sectional view of alternative embodiment of the present invention incorporating a temperature sensor.

FIG. 17 is a cross-sectional view of an embodiment in which a heating element 114 is positioned below the sleeve 116. The sleeve is thermal contact with the heating element as well as cold plate 118 and is additionally in contact with sensor mass 120. By selecting an appropriate sensor mass and thermal resistance between the mass and the sleeve, its temperature will be dynamically equivalent to the temperature of the sample solution 122 within sample well 124 to thus eliminate the need to insert a temperature sensor into the sample.

Figure 18:
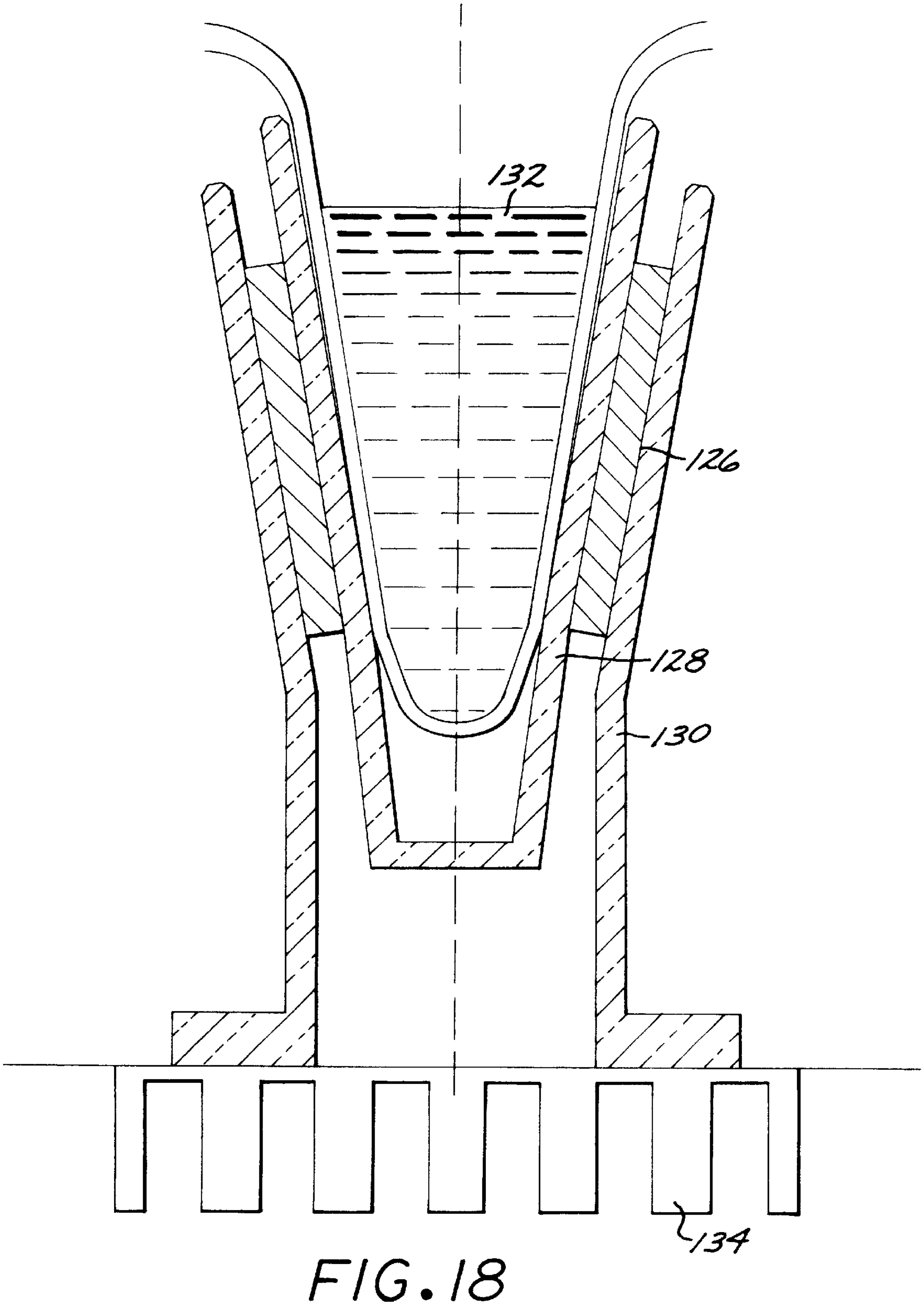
FIG. 18 is a cross-section of another alternative embodiment of the present invention.

FIG. 18 illustrates another alternative embodiment in which A Peltier device 126 is sandwiched between electrically insulative but thermally conductive ceramic cones 128, 130. The Peltier device, or thermal-electric (TE) semiconductor couples are mounted directly to both ceramic surfaces. By dynamically changing the polarity of the DC voltage supplied to the TE couples, heat can be made to flow out of the solution 132 to the outer ceramic shell 130 to an air heat exchanger 134, or conversely, heat removed from the heat exchanger can be added to the solution. A metallic sleeve (not shown) may be added to the outer surface of the outer ceramic shell to enhance heat transfer to and from the heat exchanger.

Figure 19:
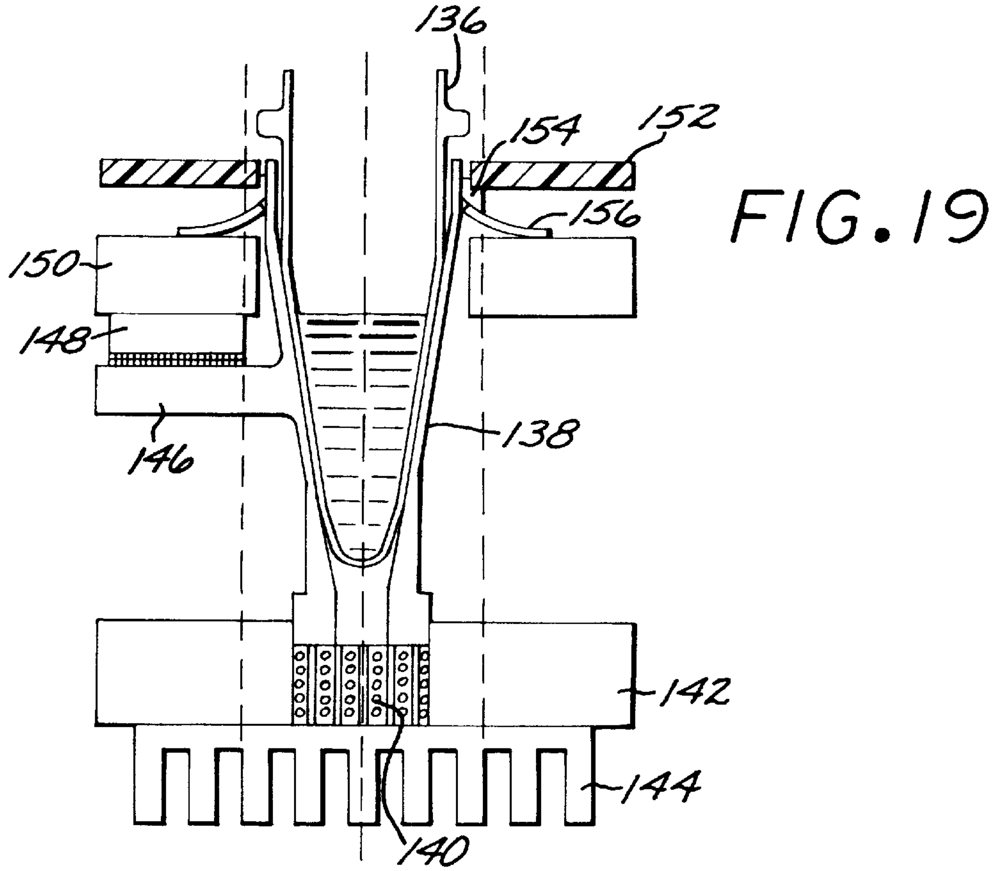
FIG. 19 is a cross-sectional view of another alternative embodiment of the present invention incorporating a temperature sensor.

FIG. 19 illustrates another configuration of the present invention in which the heating and cooling device and the temperature sensor are mounted on printed circuit boards. Sample well 136 is received in sleeve 138 which is in thermal contact with Peltier device 140 that is mounted on circuit board 142, both of which are in contact with air heat exchanger 144. The sleeve additionally includes a wing element 146 that extends between adjacent wells and serves as a thermal mass. A temperature sensor 148 in the form of an integrated circuit is mounted to a second printed circuit board 150. A cover plate 152, seal 154 and spring nut 156 maintain the chip in thermal contact with the sleeve wing. The sleeve acts as a thermal mass for dynamic similarity with the solution temperature and obviates the need to insert a sensor into the sample to provide feedback information to the controller.

Figure 20:
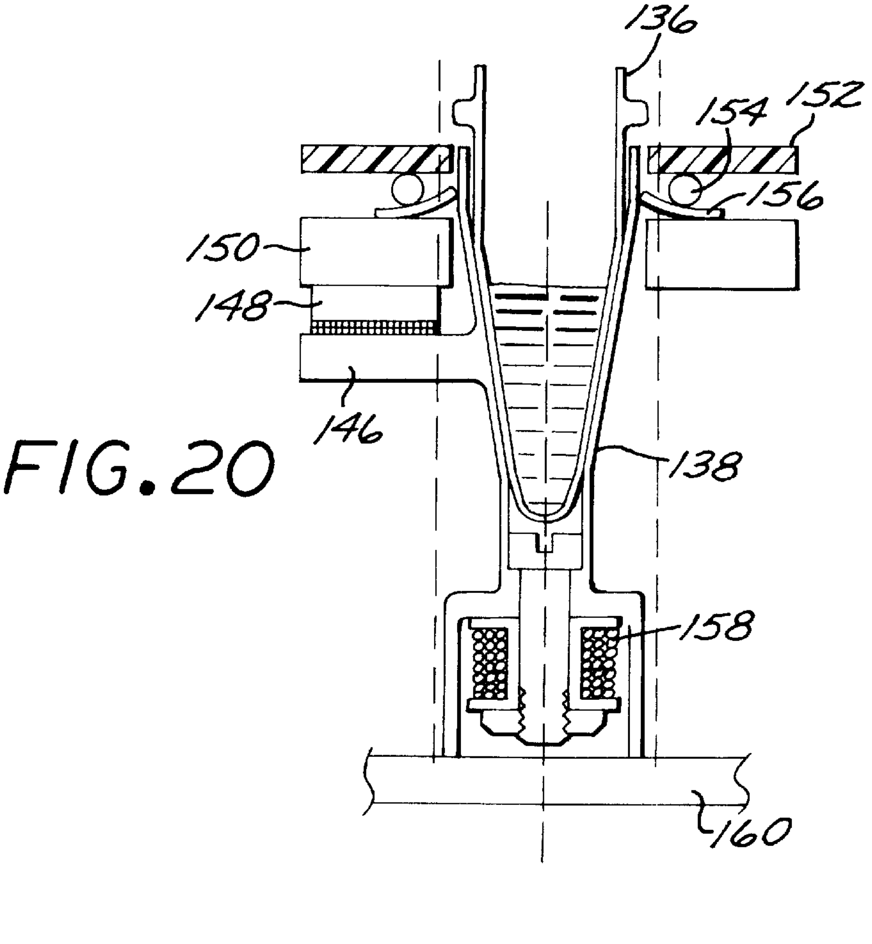
FIG. 20 is a cross-sectional view of yet another alternative embodiment incorporating a temperature sensor.

FIG. 20 illustrates an alternative embodiment in which only a single printed circuit board is employed. Sample well 136 is received in sleeve 138 which is in thermal contact with electric heating coil 158 and with cold plate 160. The sleeve additionally includes a wing element 146 that extends between adjacent wells and serves as a thermal mass. A temperature sensor 148 in the form of an integrated circuit is mounted to a printed circuit board 150. A cover plate 152, seal 154 and spring nut 156 maintain the chip in thermal contact with the sleeve wing. The sleeve acts as a thermal mass for dynamic similarity with the solution temperature and obviates the need to insert a sensor into the sample to provide feedback information to the controller.

Figure 21:
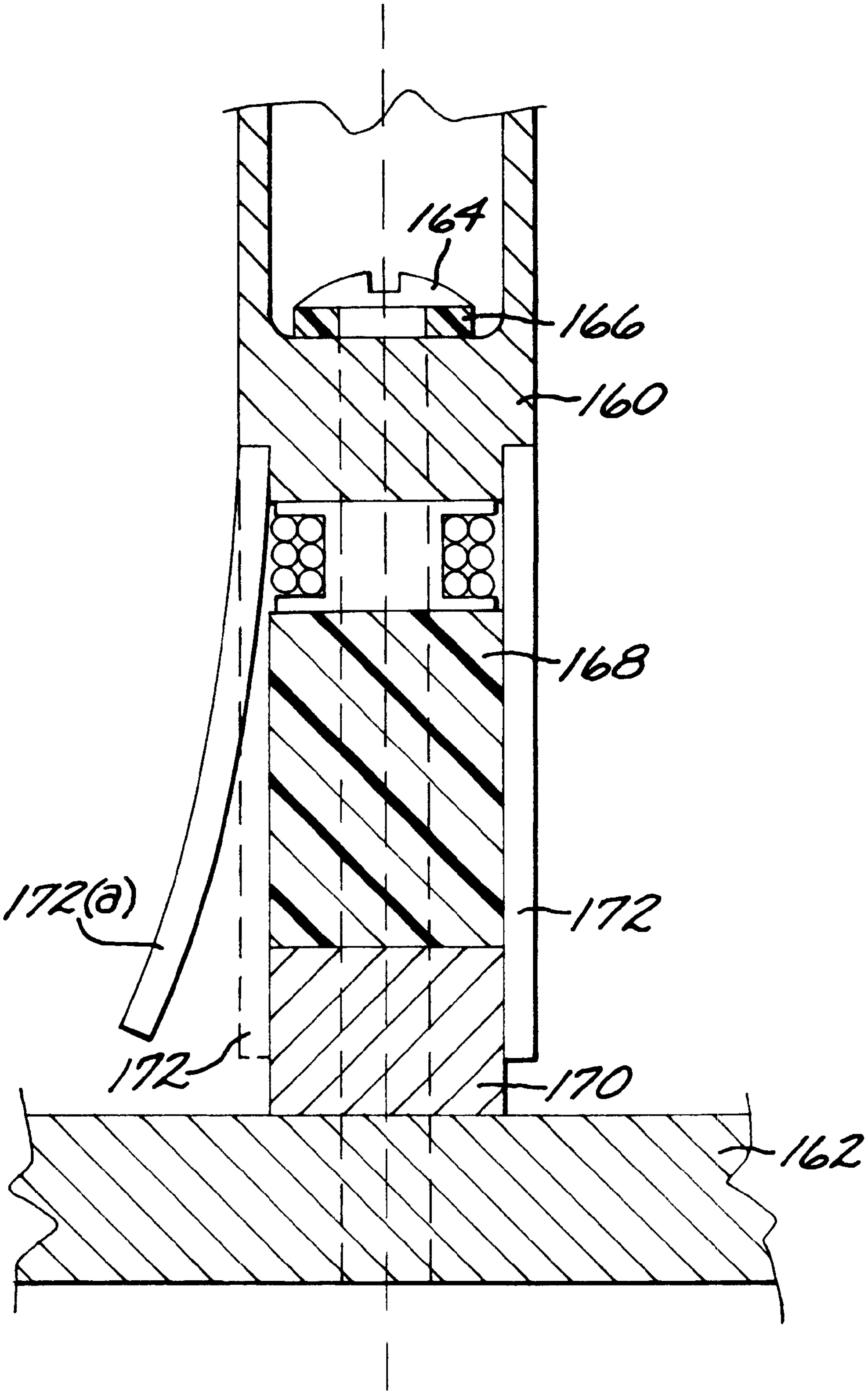
FIG. 21 is an alternative embodiment of the present invention.

FIG. 21 illustrates and alternative embodiment in which variable thermal contact with the cold plate is provided. The base of sleeve 160, which receives a sample well, is affixed to cold plate 162 via a tie screw 164 that extends through an insulting washer 166, the base of the sleeve, an insulation block 168, a metal standoff element 170 and into cold plate. A bimetallic element 172 is in thermal contact with the base of the sleeve as well as heating element 174. The bimetallic element may have a semi-cylindrical shape or may consist of multiple strips or fingers. In its deactivated state it presses against the metal standoff element which is in thermal contact with the cold plate. Upon energization of the heating element, heat is transferred to sample well and to the bimetallic element which causes it to deflect outwardly (172*a*) to thereby disengage from the metal plug element. De-energization of the heating coil will allow the bimetallic element to cool and will reassume its un-deflected state to re-engage the metal plug element to re-establish rapid heat flow to the cold plate. A Nitinol material may be substituted for the bimetallic element.

In operation, the titration plate 19 of samples is placed on the top of the heating device 12 such that the individual sample wells 18 are received within the corresponding sleeves 14. The resiliency of the slotted configuration 16 of the sleeves and/or the resiliency of the surrounding elastomeric material 24 cause the sleeves 14 to make intimate contact with the sample wells 18 and hence thermal contact is achieved. After termination of heating, heat absorbed by an individual well in the titration plate and the sample contained therein is conducted to the cold plate 20 and removed by electronic cooling (Peltier effect) or by refrigerated coolant circulating there-through, thus refreezing the thawed samples. By virtue of the well and titration plate geometry, a greater portion of generated heat during thawing is absorbed in the material within the well than is absorbed in the cold plate 20.

The controller 30 is programmed by the operator to energize a selected heating element 26 or elements causing the temperature of the corresponding sleeve 14 to quickly rise. Optionally, the sleeve 14 is simultaneously decoupled from the cold plate to further expedite the thawing process. The heat conducted to the sample well 18 by the sleeve 14 causes the temperature of material 28 contained therein to increase. Denergization of the heating element 26 causes the residual heat to be conducted away from the sample well 18 via the sleeve 14 to allow any remaining material to cool. Throughout this entire process, the temperature of the samples contained in all other sample wells remain undisturbed. Similar procedures are used to actuate the alternative heat and cooling mechanisms described above. The controller may be subject to manual, analog, or numerical operation.

Figure 22:
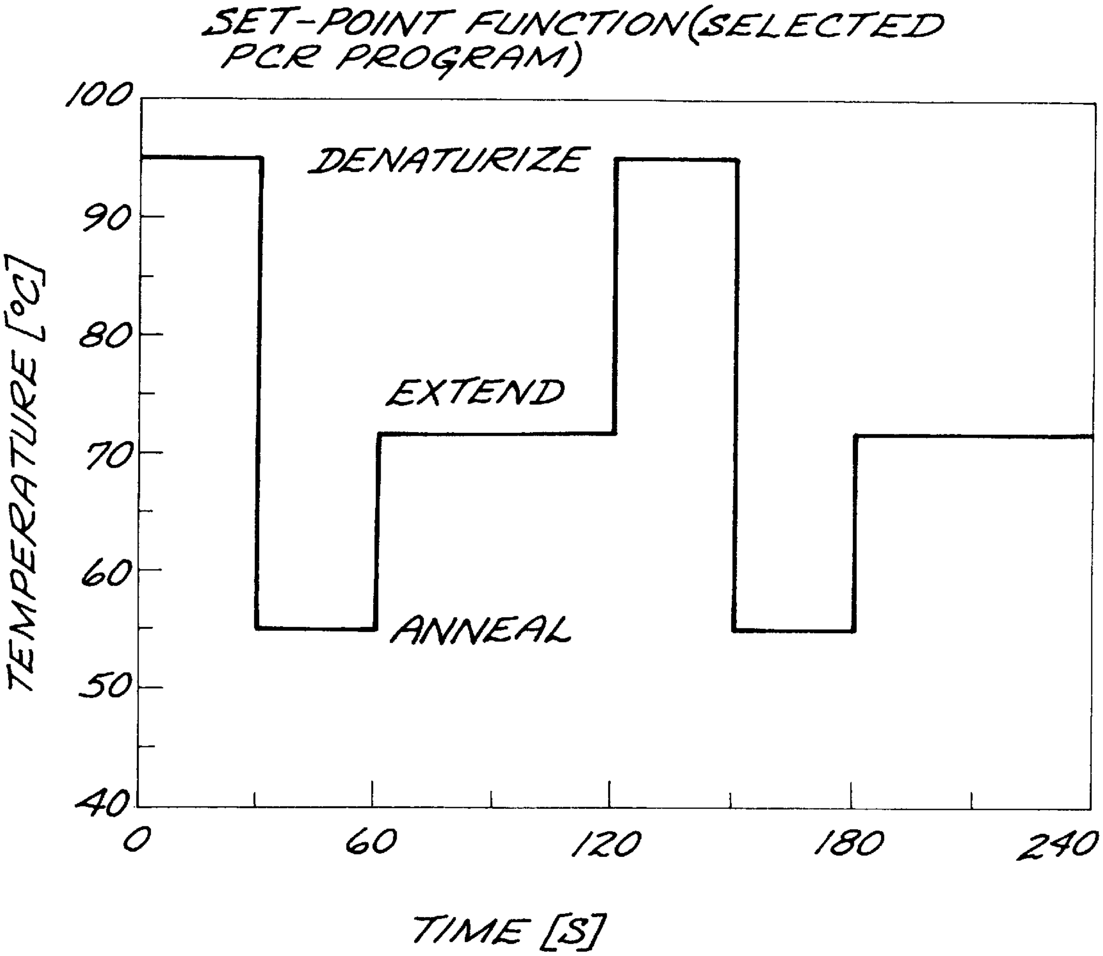
FIG. 22 is a graph depicting the set points for a device of the present invention as may be used for a PCR and DNA amplification.
Figure 23:
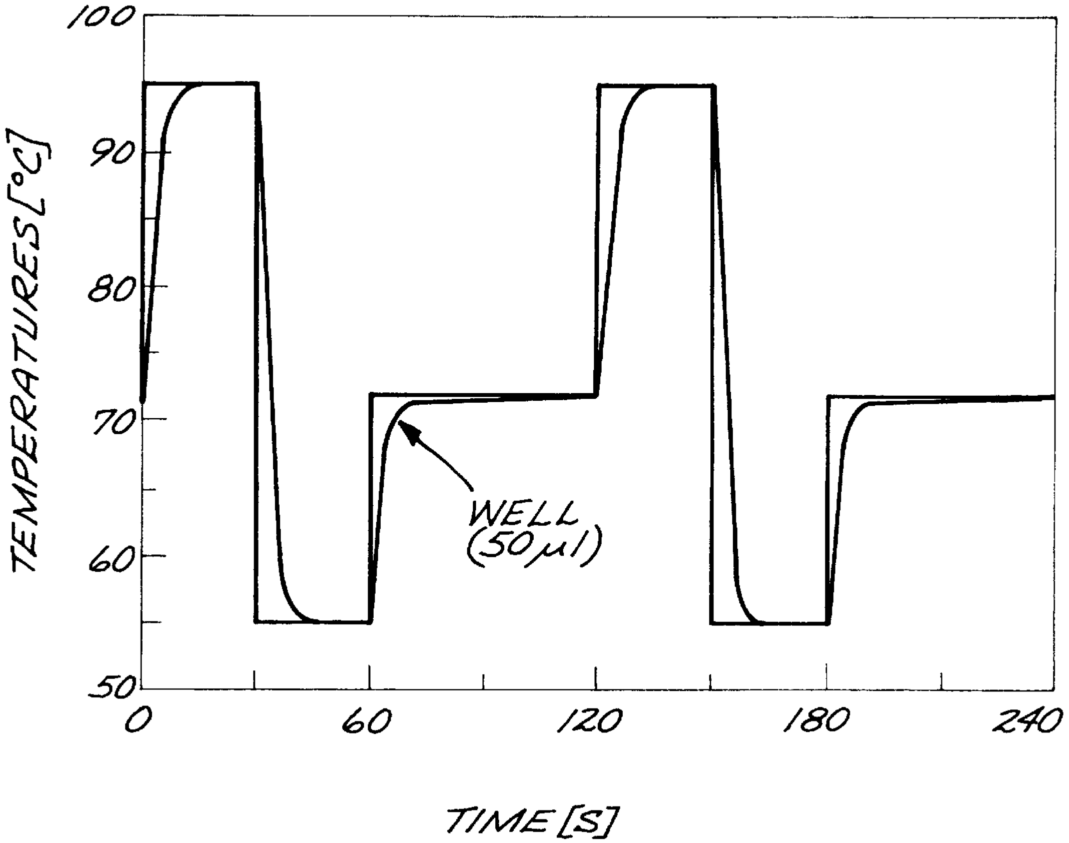
FIG. 23 is a graph depicting temperature set points and actual temperature for a sample being cycled by a device of the present invention.

FIG. 22 illustrates a representative example of a thermal cycle (PCR program) that the thermal cycler of the present invention may be called upon to subject an individual sample or individual samples to. The graph depicts the programmed time varying set points that the device strives to achieve. Temperature feedback allows the heating and cooling mechanisms to be activated and deactivated so as to follow the curve 174 as closely as possible. FIG. 23 is a representation of how the actual temperature 176 may lag slightly behind the set points. A ramping speed of 4C/sec for a 50 microliter sample is readily attainable with the thermal cycler of the present invention. Moreover, each of the sample wells in a titration plate can be simultaneously be subjected to their own PCR programs without regard to the programs being followed by adjacent sites.

While a particular form of the invention has been illustrated and described, it will also be apparent to those skilled in the art that various modifications can be made without departing from the spirit and scope of the invention. For example, any of various heating means, including but not limited to those described and illustrated herein can be employed to selectively heat each sample well while any of various cooling means can be utilized to cool the samples. Additionally, any temperature sensing means, including direct insertion of a sensor into the sample, may be employed in combination with any of the heating and cooling mechanisms to provide feedback information to a controller. Accordingly, it is not intended that the invention be limited except by the appended claims.

What is claimed is:

1. A device for simultaneously subjecting samples contained within individual sample wells of a multi-well titration plate to different preselected programs of temperature variations, comprising:

a fixed array of sleeves dimensioned and arranged to individually receive each of said sample wells in a titration plate;

an individually controllable heating mechanism associated with each sleeve which upon activation, individually and exclusively causes the sample contained in the sample well received in such sleeve to increase in temperature;

a cooling mechanism associated with each of sleeve which is capable of withdrawing heat from a sample contained in the sample well received in such sleeve so as to decrease its temperature;

a controller for controlling each of said heating mechanism such that samples contained within each of said sample wells may simultaneously be subjected to an individually preselected temperature variation program.

2. The device of claim 1, wherein said controller additionally controls each of said cooling mechanisms.

3. The device of claim 1, wherein each of said individually controllable heating mechanism comprises a heating element in thermal contact with one of said sleeves and said cooling mechanism comprises a heat sink.

4. The device of claim 3, wherein said heat sink comprises a cold plate.

5. The device of claim 3, wherein said heat sink comprises an air heat exchanger.

6. The device of claim 1, wherein said cooling mechanism comprises a separate, individually controllable cooling device for each sample well.

7. The device of claim 6, wherein said heating and cooling mechanism associated with each sleeve comprises a Peltier device.

8. The device of claim 7, further comprising a heat sink in thermal contact with said Peltier device.

9. The device of claim 1, wherein said cooling mechanism comprises a separate deflectable thermal conductor that is in thermal contact with each of said heating mechanisms, wherein such conductor is configured to be in thermal contact with a heat sink while in its undeflected state and to break thermal contact with said heat sink upon deflection, and wherein deflection is caused by heat generated by said heating mechanism.

10. The device of claim 9, wherein said deflectable thermal conductor comprises a bimetallic element.

11. The device of claim 9, wherein said deflectable thermal conductor comprises a nitinol material.

* * * * *